United States Patent [19]

Babej et al.

[11] 4,024,181
[45] May 17, 1977

[54] ANALOGUES OF PROSTANOIC ACIDS

[75] Inventors: Milos Babej, Frankfurt am Main; Wilhelm Bartmann, Neuenhain, Taunus; Gerhard Beck, Frankfurt am Main; Ulrich Lerch, Hofheim, Taunus, all of Germany

[73] Assignee: Hoechst Aktiengesellschaft, Frankfurt am Main, Germany

[22] Filed: Nov. 19, 1974

[21] Appl. No.: 525,174

[30] Foreign Application Priority Data

Nov. 21, 1973   Germany ........................... 2357953

[52] U.S. Cl. ........................ 260/514 D; 260/240 R; 260/327 M; 260/340.7; 260/340.9; 260/468 D; 260/473 A; 260/520 B; 424/305; 424/317
[51] Int. Cl.² .................................... C07C 177/00
[58] Field of Search ............. 260/468 D, 514 D, 69

[56] References Cited

UNITED STATES PATENTS

| | | | |
|---|---|---|---|
| 3,853,951 | 12/1974 | Bernards et al. ................... | 260/468 |
| 3,873,607 | 3/1975 | Bernards et al. ................... | 260/514 |
| 3,884,909 | 5/1975 | Schaub et al. ..................... | 260/514 |
| 3,890,309 | 6/1975 | Finch et al. ....................... | 260/468 |

FOREIGN PATENTS OR APPLICATIONS

| | | | |
|---|---|---|---|
| 784,809 | 1/1972 | Belgium .............................. | 260/468 |
| 2,401,761 | 7/1974 | Germany ............................ | 260/468 |
| 7,209,738 | 1/1973 | Netherlands ....................... | 260/468 |

OTHER PUBLICATIONS

Bartmann et al., Tet. Letters, 2441 (1974).

*Primary Examiner*—Robert Gerstl
*Attorney, Agent, or Firm*—Curtis, Morris & Safford

[57] ABSTRACT

The present invention relates to novel not naturally occuring analogues of prostanoic acids of the formula

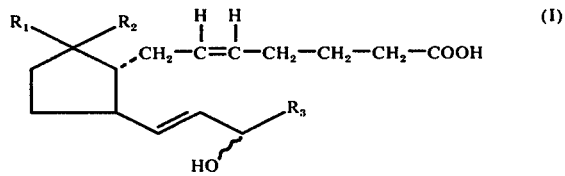

as well as a process for their preparation. The compounds of the invention have valuable pharmacological properties similar to those of the natural prostaglandins and therefore can be used as medicaments.

3 Claims, No Drawings

ANALOGUES OF PROSTANOIC ACIDS

The present invention relates to novel, not naturally occurring analogues of prostanoic acids and to a process for their manufacture.

Prostaglandins are a group of natural substances which were isolated from different animal tissues. In mammals they are responsible for a great number of physiological actions. The natural prostaglandins have a carbon skeleton containing, in general, 20 carbon atoms and are distinguished, above all, by the major or minor content of hydroxyl groups or double bonds in the cyclopentane ring; (the structure and action of prostaglandins are described, i.a. in M. F. Cuthbert "The Prostaglandins, Pharmacological and Therapeutic Advances", William Heinemann Medical Books Ltd., London 1973).

The syntheses of not naturally occurring analogues of prostanoic acids in which the great variety of the pharmacological actions of the natural prostanoic acids is differentiated, grow more and more important.

The present invention relates to novel, not naturally occurring analogues of prostanoic acids of the formula I

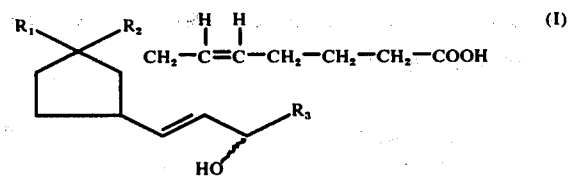

in which the symbols have the following meaning: $R_1$ and $R_2$ together represent oxygen or each of them represents hydrogen or a hydroxyl group, $R_1$ and $R_2$ being different, $R_3$ stands for a saturated, linear or branched alkyl radical of 1 to 10 carbon atoms and the alkyl radical may be substituted by an O-alkyl radical of 1 to 5 alkyl carbon atoms, or a saturated cycloalkyl radical of 3 to 7 ring members or an aryl or furyl radical and these radicals may be substituted by one or several alkyl groups of 1 to 3 carbon atoms, and the cycloalkyl radical may also be substituted by fluoro atoms.

This invention also relates to the physiologically acceptable salts thereof with organic and inorganic bases.

Further objects of the invention are processes for the manufacture of the novel, not naturally occurring analogues of prostanoic acids of the general formula I and the physiologically acceptable salts thereof with organic and inorganic bases and pharmaceutical preparations which contain these active substances.

The process of the invention comprises eliminating the ketal groups in the alcohols of the formula XVI

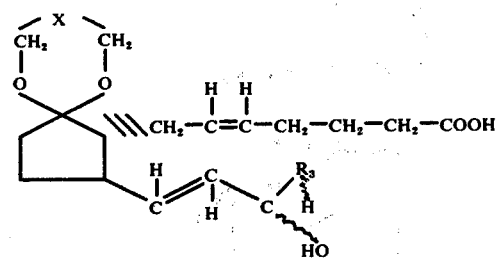

in which X stands for a simple bond or a —CH$_2$— or a

group and $R_3$ is defined as in formula I, either by careful, acid-catalytic hydrolysis or by reketalization in the presence of a great excess of a ketone and, optionally, reducing the compounds so obtained of the formula I in which $R_1$ and $R_2$ together stand for oxygen, to compounds of the formula I in which $R_1$ and $R_2$ each stands for hydrogen or a hydroxyl group, with a complex metal hydride and, if desired, converting them into the physiologically acceptable salts.

The alcohols of the formula XVI are preferably manufactured according to the following method which comprises a. reacting the lactol of the formula II

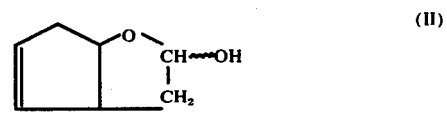

in the presence of an acid catalyst and ethylene thioglycol in an aprotic solvent, at a temperature ranging from 20° to 140° C, in an inert atmosphere to yield the thioketal of the formula III

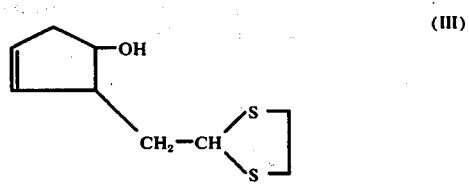

b. oxidizing the thioketal of the formula III in dimethyl sulfoxide with a carbodiimide, in the presence of an acid catalyst, to a mixture of isomeric unsaturated ketones of the formula IV and V

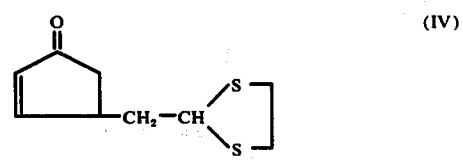

and

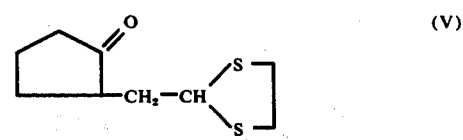

c. reacting the mixture of the ketones IV and V under alkaline conditions with cyanide ions, whereupon the ketone IV is isomerised to the ketone V and the cyan ketone of the formula VI is simultaneously formed,

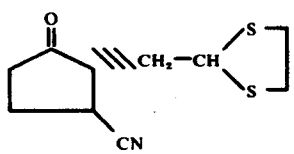

(VI)

d. heating the cyan ketone of the formula VI in a manner known per se with a diol of the general formula VII

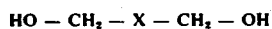

(VII)

in which X is a simple bond or a —CH$_2$— or

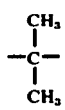

group, in the presence of acid catalysts in an aprotic solvent, whereupon cyan ketals of the general formula VIII

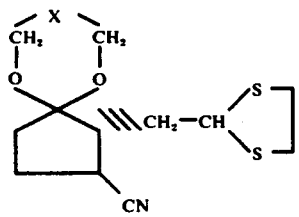

(VIII)

are obtained, e. reducing compounds of the formula VIII at a temperature ranging from —40° to +40° C with 1 to 1.5 mols of a complex metal hydride in aprotic, absolute solvents to compounds of the formula IX

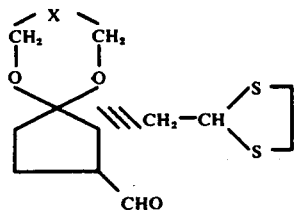

(IX)

in which X is defined as in the formula VII, f. reacting the aldehydes of the formula IX with a phosphonate of the formula X

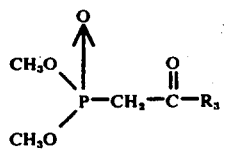

(X)

in which R$_3$ is defined as in the formula I, to yield the unsaturated ketones of the formula XI

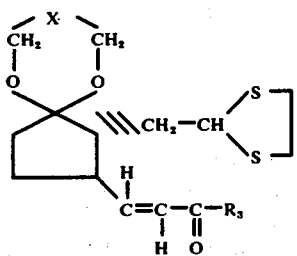

(XI)

in which X is defined as in the formula VII and R$_3$ is defined as in the formula I, g. reducing the ketones of the formula XI with a complex metal hydride to an epimeric mixture of the alcohols of the formula XII

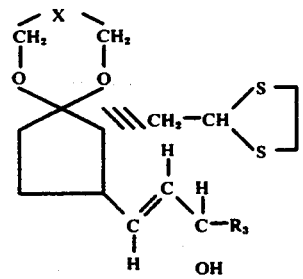

(XII)

in which X and R$_3$ are defined as in the formula VII or I, h. converting the alcohols of the formula XII as epimer mixtures, or after the separation of the epimers by the acid catalyzed addition of 2,3-dihydropyrane, into the tetrahydropyranyl ethers of the formula XIII

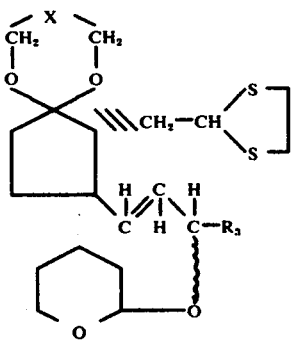

(XIII)

in which X and R$_3$ are defined as in the formula VII or I, i. converting the ethers of the formula XIII by heating with methyl iodide in acetone or in dimethyl formamide in the presence of an acid binding agent into the aldehyde ethers of the formula XIV

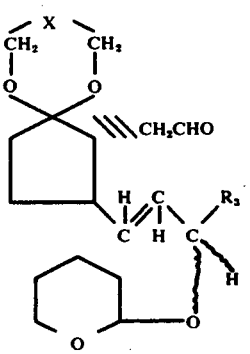

(XIV)

in which X and R₃ are defined as in the formula VII or I, j. reacting the aldehyde ethers of the formula XIV with the ylide of 4-carboxybutyltriphenyl-phosphonium bromide in a solution of sodium hydride in dimethyl sulfoxide to yield the acids of the formula XV

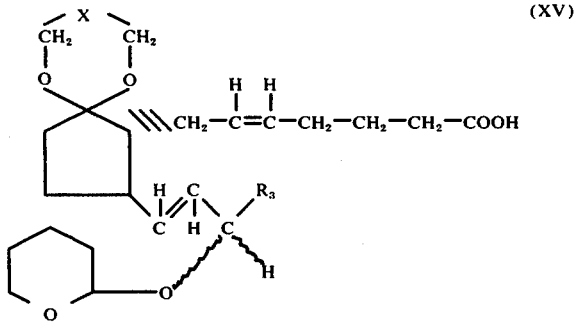

in which X and R₃ are defined as in the formula VII and I, k. eliminating the tetrahydropyranyl ether protective group by careful, acid hydrolysis, whereupon alcohols of the formula XVI

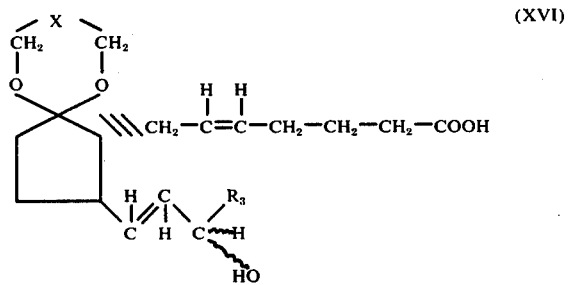

in which X and R₃ are defined as in the formula VII or I, are obtained and l. eliminating the ketal grouping in the alcohols of the formula XVI either by careful, acid catalyzed hydrolysis or by reketalization in the presence of a great excess of a ketone and, optionally, reducing the compounds of the formula I so obtained in which R₁ and R₂ together stand for oxygen, to compounds of the formula I in which R₁ and R₂ each stands for hydrogen or a hydroxyl group, with a complex metal hydride and, optionally, converting these compounds into the physiologically acceptable salts thereof.

Among the radicals named for the substituent R₃, the alkyl radical of 3 to 8 carbon atoms, the cycloalkyl radical of 3 to 7 carbon atoms, as well as phenyl or phenyl substituted by one or several methyl groups, and the cyclobutyl radical, substituted by one or several fluorine atoms, especially the 3,3,4,4-tetrafluorocyclobutyl radical, are preferred.

The first step of the process for the manufacture of the compounds of the formula I preferably comprises the splitting of the hemiacetal of the (cis-2-hydroxycyclopent-4-enyl)-acetaldehyde of the formula II (prepared according to Paul A. Grieco J. Org. Chemistry 37, (1972), page 2363) with ethylene thio glycol to yield the ethylene thioacetal of the (cis-2-hydroxycyclopent-4-enyl)-acetaldehyde of the formula III in the presence of acid catalysts, for example, p-toluene-sulfonic acid or, preferably, boron trifluoride etherate in absolute, aprotic solvents, such as benzene or xylene or cyclohexane, preferably at the boiling temperature of the solvent and with the simultaneously occuring azeotropic distillation of the water formed in the reaction. In principle, the ethylene thioglycol can be replaced by other thioglycols, for example, by propylene dithioglycol.

In general, thioacetals are so sensitive towards the usual oxidation reactants, such as chromic acid, in different solvents under acid, neutral or basic conditions, that the attempt to oxidize the OH-group of the thioacetal of the formula III selectively to the ketone of the formula IV or its isomers of the formula V is not successful even under careful conditions (cf. also Seebach in Synthesis 1, (1969), page 31). Surprisingly, the OH group in the thioacetal of the formula III can be oxidized to the (2-oxo-cyclopent-4-enyl)-acetaldehyde-thio-acetate of the formula IV without attacking the thioacetal grouping according to the indications made in Fieser-Fieser, Reagents for Organic Synthesis, John Wiley and Sons, Inc., New York, (1967), page 303 et seq., the oxidation advantageously being carried out with DMSO and a carbodiimide, preferably dicyclohexyl-carbodiimide, in the presence of an acid catalyst, preferably anhydrous ortho-phosphoric acid or pyridinium trifluoroacetate. According to the duration of the reaction time, the double bond in the 4-position is simultaneously shifted to the 5-position yielding the (2-oxo-cyclopent-5-enyl)-acetaldehyde-thio-acetal of the formula V.

The ketone of the formula V can be isolated in pure form, however, it is advantageous to use the crude mixture of the ketones IV and V obtained by the oxidation described above directly for the following reaction in which they are reacted with cyanid ions to the (5-cyano-2-oxo-cyclo-pentyl)-acetaldehyde thioacetal of the formula VI under alkaline conditions. Under these conditions the residual compound IV is isomerized to the compound V. The cyanide ions are additoned in a manner known per se, for example with potassium cyanide in methanol. A preferred embodiment of the invention is the conversion of compound V in methanolic solution with acetone-cyanohydrin in the presence of sodium or potassium carbonate. Related to the positions 1 and 5, the ketone of the formula VI obtained can be in the form of a mixture of the cis-trans-isomers.

However, the presence of the cis-trans-isomers is irrelevant for the configuration of the end products because in the continuation of the synthesis isomerisaton to a more stable trans-configuration is possible.

The ketone of the general formula VI is converted in a manner known per se into ketals of the general formula VIII with diols of the general formula VII in the presence of acid catalysts. As to stability, the neopentyl-ketal

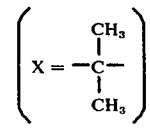

is to be preferred, whereas the ethylene ketal grouping (with X being a simple bond) can more easily be split off from the end products. As acid catalysts p-toluene-sulfonic acid or boron trifluoride etherate and as solvents benzene or xylene are especially suitable. The reaction is preferably carried out at the boiling temperature of the solvent, the water formed optionally being separated with a water separator.

The second step of the process of the invention comprises the reduction of the nitriles VIII to the aldehydes IX which is effected in a manner known per se with 1 – 1.5 mols of a complex metal hydride, preferably diisobutyl aluminum hydride, in an aprotic solvent, such as toluene or another absolute anhydrous hydrocarbon at a temperature ranging from −40° to +40° C, preferably in the range of from 0° to 10° C.

In the continued operation, the aldehydes of the general formula IX are reacted in a manner known per se according to the Horner, Emmons and Wittig method with the phosphonic acid esters of the general formula X to yield the unsaturated ketones of the general formula XI, the reaction being preferably carried out in such a manner that the sodium salt of the phosphonic acid ester of the general formula X is prepared with sodium hydride in glycol dimethyl ether and then the aldehydes of the general formula IX are added and the whole is reacted at room temperature for 2 – 6 hours. The phosphonic acid esters of the general formula X are prepared according to known methods disclosed in literature (cf., for example Corey, J. Am Chem. Soc. 88, 5654 (1966)).

The alcohols of the general formula XII are obtained in the form of their epimeric mixtures when the ketones of the general formula XI are reduced in a manner known per se with a complex metal hydride, preferably an alkali metal boranate. The alcohols of the general formula XII are especially suitable for an epimer separation, however, the further reaction can also be carried out with the epimer mixture and the epimers can be separated in the state of the end products.

The dihydropyrane is added to the tetra-hydropyranyl ethers of the general formula XIII in a manner known per se in an etheric or benzenic solution of the alcohols of the general formula XII in the presence of usual acid catalysts for example p-toluene sulfonic acid. In general, it is advantageous to purify the tetrahydropyranyl ethers of the general formula XIII obtained at this point by chromatography.

The setting free of aldehydes and ketones from thioacetals or thioketals is the object of a great number of references made in the literature because of the preparative difficulties rising therefrom (c.f., inter alia Chang in Tetrahydron Letters No. 19, page 1989 (1972)). Especially the preparation of the relatively sensitive aliphatic aldehydes is difficult, the more so when the same molecule contains especially acid-labile protective groups, for example the tetra-hydropyranyl ether group. Especially in the method described by Chang, in which the thioketal is split with methyl iodide in methanol, hydrogen iodide is set free which itself splits off the tetrahydropyranyl ether grouping required as a protective group. Surprisingly, the aldehydes of the general formula XIV are formed in practically quantitative yield by adding acid binding agents, preferably calcium carbonate, to a solution of the thioacetals of the general formula XIII in dimethylformamide after heating for 1 – 5 hours at 30° – 70° C, preferably 50° C, with methyl iodide, whereby the tetrahydropyranyl protective group is obtained. When acetone is used instead of dimethylformamide, the yield is slightly reduced.

The aldehyde ethers of the general formula XIV so prepared can be reacted without further purification in a manner known per se to yield the carboxylic acids of the general formula XV. The Wittig reaction is preferably carried out according to the prescription disclosed in J. Org. Chem. 28, 1128 (1963).

The ether protective groups are split off by careful acid hydrolysis of the tetrahydropyranyl ether grouping in a manner known per se, preferably in a 2% aqueous-alcoholic oxalic acid solution at 20° – 50° C, or by heating for 1 – 2 hours in 60 – 70% acetic acid to 50° C, which operation yields the carboxylic acids of the general formula XVI. The last step of the synthesis of the invention comprises the careful, acid hydrolysis of the ketal grouping of the compounds of the formula XVI to yield the compounds of the general formula I in which $R_1$ and $R_2$ together stand for oxygen. The ketal grouping can also be split off by reketalization of compound XVI to compound I in which $R_1$ and $R_2$ together stand for oxygen in the presence of a great excess of a ketone, preferably acetone, in the presence of acid catalysts, such as p-toluene-sulfonic acid.

The reduction to the compounds of the formula I in which $R_1$ and $R_2$ each stands for hydrogen or a hydroxyl group is effected in a manner known per se with a complex metal hydride, preferably with a metal boranate, for example sodium boron hydride, in aqueous-alcoholic solution. A mixture of the $9\alpha$, $\beta$-epimeric alcohols is obtained. The epimers can be separated in the usual manner, for example by thin layer chromatography or distribution chromatography.

If the epimers are not separated at the stage of the alcohols of the general formula XII, the compounds of the general formula I in which $R_1$ and $R_2$ together stand for oxygen can be used to separate the epimers of the alcohols in the 15-position (as to the nomenclature of the prostaglandins c.f. N. Andersen, Annals of the New York Academy of Sciences, Volume 180, Prosta-glandins, page 14).

Furthermore, a racemate separation can be effected at the stage of the acids of the general formula XV or of the general formula I in the usual manner by the formation of salts with optically active bases.

The compounds so synthesized are distinguished by good spasmogenic, bronchodilatent and hypotensive properties and have a considerably greater stability as compared with the natural prostaglandins E, F and A. Therefore, they can be used as medicaments.

The compounds of the invention of the general formula I can be used as free acids or in the form of their physiologically acceptable inorganic or organic acids. Suitable salts are, for example, benzylammonium salts, triethaolammonium salts or morpholine salts as well as alkali metal salts.

The acids and salts can be administered in the form of their aqueous solutions or suspensions or also as solutions in pharmacologically acceptable organic solvents, for example mono or multivalent alcohols, dimethyl sulfoxide or dimethylformamide also in the presence of pharmacologically acceptable polymer carriers, for example polyvinyl pyrrolidone.

Suitable preparations are the usual galenic infusion or injection solutions and tablets, preferably, however, preparations which can be administered locally, such as pastes, emulsions, suppositories or aerosols.

For oral administration, forms such as tablets, dragees or gelatin capsules, the usual pharmaceutical carriers such as starch, lactose, tragacanth and magnesium carbonate may be used with addition of other suitable substances such as magnesium stearate. The daily dose used for oral administration is about 5 mg to 500 mg; preferably 5 to 100 mg. A dosage unit form preferably contains 5 mg to 50 mg of a compound of the invention.

The compounds can be used alone or in combination with other pharmacologically active substances, for example diuretics or antidiabetics.

The compounds of the formulae XVI, XV, XIV, XIII, XII, XI, IX, VIII, VI, V, IV and III are valuable intermediates for the synthesis of the compounds of the invention of the formula I.

The following examples illustrate the invention:

EXAMPLE 1

(cis-2-hydroxy-cyclopent-4-enyl)-acetaldehyde-ethylene-thioacetal (formula III)

20 g of the hemiacetal of (cis-2-hydroxy-cyclopent-4-enyl)-acet-aldehyde (prepared according to Paul A. Grieco, J. Org. Chemistry 37 (1972), page 2363) were boiled under reflux in 200 ml of absolute benzene with 14.5 ml of ethylene thioglycol and 0.6 ml of borontrifluoride etherate for 3 hours with a water separator under nitrogen. The cooled solution was washed twice with 50 ml of 2 N sodium carbonate solution, twice with 50 ml of water, dried over $Na_2SO_4$ and condensed. 28 g of compound III were obtained which crystallized at $-18°$ C when covered with petroleum ether ($40°-80°$).

The melting point was $25°-30°$ C.
NMR spectrum:
5.7 ppm, 2 protons, multiplet
4.3-4.8 ppm, 2 protons, multiplet
3.25 ppm, 1 proton, singlet

EXAMPLE 2

(2-oxo-cyclopent-4-enyl)-acetaldehydeethylene-thioacetal IV (2-oxo-cyclopent-5-enyl)-acetaldehydeethylene-thioacetal V 28 g of (cis-2-hydroxy-cyclopent-4-enyl)acetaldehydeethylene-thioacetal were dissolved in 200 ml of benzene and added to a solution of 144 g of dicyclohexylcarbodiimide in 200 ml of dimethyl-sulfoxide which contained 72 ml of a solution of 7.8 g of $H_3PO_4$ in 100 ml of dimethyl sulfoxide, and stirred for 8 hours at room temperature. Thereafter, the solution was diluted with 600 ml of diethyl ether, cooled to $0°$ C and stirred with 72 g of oxalic acid in 300 ml of methanol until the gas development had finished. The precipitated dicyclohexyl urea was filtered off and the remaining solution was washed twice with 50 ml portions of 2 N sodium carbonate solution and four times with 50 ml portions of water, dried over sodium sulfate and condensed. 28 g of oil were obtained.

UR spectrum:
strong ketone bands at 1700 $cm^{-1}$,
lighter ketone bands at 1740 $cm^{-1}$.

EXAMPLE 3

(2-oxo-cyclopent-5-enyl)acetaldehydeethylene-thioacetal V 11 g of the mixture of the ketones described in Example 2 were chromatographed on silica gel (according to Merck).

6.7 g of pure compound V were obtained.
UR spectrum:
ketone bands at 1700 $cm^{-1}$,
double bond bands at 1640 $cm^{-1}$
NMR spectrum:
7.5 ppm, 1 proton, multiplet
5.7 ppm, 1 proton, triplet
3.2 ppm, 4 protons, singlet

EXAMPLE 4

(5-cyano-2-oxo-cyclopentyl)acetaldehyde-ethylenethioacetal VI 18 g of the mixture of (2-oxo-cyclopent-4-enyl)acetaldehyde-ethylenethioacetal and (2-oxo-cyclopent-5-enyl)acetaldehyde-ethylene-thioacetal according to stage 2 were dissolved in 150 ml of methanol and 9.2 g of acetonecyanohydrin and a solution of 7.5 g of $Na_2CO_3$ in 20 ml of water were added. After stirring for 3 hours at room temperature, all the solvent was distilled off in vacuo, the residue was taken up in 500 ml of diethyl ether and 100 ml of $H_2O$, and the ether phase was washed twice with 50 ml of $H_2O$, dried over sodium sulfate and condensed. The residue was triturated with a small amount of ether and 12 g of crude product were obtained which melted at about $98°$ C.

NMR spectrum:
4.85 ppm, 1 proton, triplet
3.25 ppm, 4 protons, singlet
UR spectrum:
2240 $cm^{-1}$ (nitrile)
1735 $cm^{-1}$ (ketone)

EXAMPLE 5

2-(3'3'-dimethylpropylene-ketal) of the (5-cyano-2-oxo-cyclopentyl)acetaldehyde-ethylenethioacetal VIII 12 g of (5-cyano-2-oxo-cyclopentyl)acetaldehyde-ethylenethioacetal of stage 4 were heated on a water separator in 400 ml of absolute toluene with 8.4 g of 3,3-dimethyl-1,3-propylene glycol and 360 mg of p-toluenesulfonic acid for 6 hours under nitrogen, washed with saturated sodium bicarbonate solution and water after cooling and the solvent was distilled off in vacuo over sodium sulfate after drying.

18.5 g of crude product were obtained which was filtered over (according to Merck)
silica gel in 9 parts of cyclohexane and 1 part of ethyl acetate.

14.9 g of pure compound VIII were obtained.
NMR spectrum:
5.9 ppm, 1 proton triplet
3.5 ppm, 4 protons singlet
3.25 ppm, 4 protons singlet
1.15 ppm, 3 protons singlet
0.7 ppm, 3 protons singlet

EXAMPLE 6

7-[(1,3-dithia-2-cyclopentyl)methyl]-3,3-dimethyl-1,5-dioxaspiro[5,4]-dec-8-yl-aldehyde IX 10.9 g of the 2-(3'3'-dimethylpropyleneketal) of (5-cyano-2-oxo-cyclopentyl)acetaldehyde-ethylenethioketal were dissolved in 250 ml of absolute toluene and cooled to $0°$ C. During 45 minutes, 10 ml of diisobutylaluminum hydride in 70 ml of absolute toluene were added dropwise and stirred for 1½ hours at $0°$ $-5°$ C. Thereafter, 10 ml of methanol, 10 ml of glacial acetic acid and 100 ml of $H_2O$ were carefully added dropwise, the mixture was stirred for 1 hour at room temperature, 300 ml of diisopropyl ether were added and the suspension was filtered over a clarifying filter. The water phase was separated, the organic phase was washed three times with water, dried and condensed.

10.5 g of aldehyde IX were obtained.

NMR spectrum:
9.4 ppm, 1 proton, doublet
5.9 ppm, 1 proton, triplet
3.5 ppm, 4 protons, singlet
3.25 ppm, 4 protons, singlet
1.15 ppm, 3 protons, singlet
0.75 ppm, 3 protons, singlet
UR spectrum: 1720 cm$^{-1}$

EXAMPLE 7

1-[7(1,3-dithia-2-cyclopentyl)methyl]-3,3-dimethyl-1,5-dioxaspiro [5,4]-dec-8-yl]-trans-1-octene-3-one XI 380 mg of NaH were suspended in 50 ml of glycoldimethyl ether and 2.88 g of dimethyl-2-oxo-heptylphosphonate in 10 ml glycoldimethyl ether were slowly added dropwise. After 1½ hours the precipitate formed was diluted with 20 ml of glycoldimethyl ether and 3.5 g of 7-[(1,3-dithia-2-cyclopentyl)methyl]-3,3-dimethyl 1,5-dioxaspiro[5,4]-dec-8-yl-aldehyde of stage 6 in 25 ml of glycoldimethyl ether were added dropwise and stirred for 2½ hours at room temperature. Just as much glacial acetic acid was added so that a sample reacted neutrally in water, 3 spatula tips covered with animal charcoal were added and the precipitate was filtered over a clarifying filter and the filtrate was condensed in vacuo.

5.39 g of crude product were chromatographed over a silica gel column with cyclohexane-ethyl acetate 95:5 and 2.52 g. of an oil were obtained.

NMR spectrum:
6–7 ppm; 2 protons, multiplet
4.9 ppm; 1 proton, triplet
3.5 ppm; 4 protons, singlet
3.2 ppm; 4 protons, singlet
1.2 ppm; 3 protons, singlet
0.95 ppm; 3 protons, triplet
0.75 ppm; 3 protons, triplet

EXAMPLE 7b

In an analogous manner, there was prepared, by reaction with dimethyl-2-oxo-nonylphosphate 1-[7-[(1,3-dithia-2-cyclopentyl)methyl]-3,3-dimethyl-1,5-dioxaspiro[5,4]-dec-8-yl]-trans-1-decene-3-one.

The NMR spectrum of this substance is practically identical qualitatively with the substance described above which has 2 carbon atoms less.

EXAMPLE 7c

In an analogous manner, there was prepared, by reaction with dimethyl-2-(5-methylfuryl)-2-oxoethylphosphate, 1-[7-[(1,3-dithia-2-cyclopentyl)methyl]-3,3-dimethyl-1,5-dioxaspiro[5,4]-dec-8-yl]-3-(5-methylfuryl)-trans-1-propene-3-one.

NMR spectrum:
6.1–7.4 ppm; 4 protons; broad signal
5 ppm; 1 proton; triplet
3.5 ppm; 4 protons; singlet
3.2 ppm; 4 protons; singlet
2.4 ppm; 3 protons; singlet
1.15 ppm; 3 protons; singlet
0.7 ppm; 3 protons; singlet

EXAMPLE 7d

In an analogous manner, there was prepared, by reaction with dimethyl-2-cyclohexyl-2-oxoethyl phosphate, 1-[7-[(1,3-dithia-2-cyclopentyl)methyl]-3,3-dimethyl-1,5-dioxaspiro[5,4]-dec-8-yl]-3-cyclohexyl-trans-1-propene-3-one.

NMR spectrum.

EXAMPLE 7e

In an analogous manner, there was prepared, by reaction with dimethyl-2-(1,1-dimethyl-3-oxapentyl)-2-oxo-ethyl phosphate, 1-[7-[(1,3-dithia-2-cyclopentyl)methyl]-3,3-dimethyl-1,5-dioxaspiro[5,4]dec-8-yl]-3-(1,1-dimethyl-3-oxapentyl)trans-1-propene-3-one.

EXAMPLE 8a

1-[7-[(1,3-dithia-2-cyclopentyl)methyl]-3,3-dimethyl-1,5-dioxaspiro[5,4]-dec-8-yl]-trans-1-octene-3-ole XII 1.26 g of sodium boron hydride were dissolved in 1.6 ml of H$_2$O and 16 ml of methanol, cooled to 0° C, and 2.52 g of [7-[(1,3-dithia-2-cyclopentyl)methyl]-3,3-dimethyl-1,5-dioxaspiro[5,4]-dec-8-yl]-trans-1-oxtene-3-one, dissolved in 50 ml of methanol, were added dropwise, and the solution was stirred for 15 hours at 0° C and for 2 hours at room temperature. The reaction mixture was neutralized with glacial acetic acid, the solvent was distilled off in vacuo, the residue was taken up in ether, washed with water, dried and condensed.

The crude product was filtered and condensed in cyclohexane/ethyl acetate 95:5 over a silica gel column 14 cm high and having a 2 cm diameter.

2.6 g of colorless oil were obtained.

R$_f$ = 0.62 (silica gel according to Merck/cyclohexane/ether 1:1).

UR spectrum: no ketone bands at 1695 cm$^{-1}$.

EXAMPLE 8b

In an analogous manner there was prepared, from 1-[7-[(1,3-dithia-2-cyclopentyl)methyl]-3,3-dimethyl-1,5-dioxa-spiro[5,4]-dec-8-yl]-trans-1-decene-3-one, 1-[7-[(1,3-dithia-2-cyclopentyl)methal]-3,3-dimethyl-1,5-dioxa-spiro[5,4]-dec-8-yl]-trans-1-decene-3-ole, and from

EXAMPLE 8c

1-[7-[(1,3-dithia-2-cyclopentyl)methyl]-3,3-dimethyl-1,5-dioxa-spiro[5,4]-dec-8yl]-3-(5-methylfuryl)-trans-1-propene-3-one, 1-[7-[(1,3-dithia-2-cyclopentyl)methyl]-3,3-dimethyl-1,5-dioxa-spiro[5,4]-dec-8-yl]-3-(5-methylfuryl)-trans-1-propene-3-ole, and from

EXAMPLE 8d

1-[7-[(1,3-dithia-2-cyclopentyl)methyl]-3,3-dimethyl-1,5-dioxa-spiro[5,4]-dec-8-yl]-3-cyclohexyl-trans-1-propene-3-one, 1-[7-[(1,3-dithia-2-cyclopentyl)methyl]-3,3-dimethyl-1,5-dioxa-spiro[5,4]-dec-8-yl]-3-cyclohexyl-trans-1-propene-3-ole, and from

EXAMPLE 8e

1-[7-[(1,3-dithia-2-cyclopentyl)methyl]-3,3-dimethyl-1,5-dioxa-spiro[5,4]-dec-8-yl]-3-(1,1-dimethyl-3-oxapentyl)-trans-1-propene-3-one,
1-[7-[(1,3-dithia-2-cyclopentyl)methyl]-3,3-dimethyl-1,5-dioxa-spiro[5,4]-dec-8-yl]-3-(1,1-dimethyl-3-oxapentyl)-trans-1-propene-3-ole.

EXAMPLE 9a

1-[7-[(1,3-dithia-2-cyclopentyl)]-3,3-dimethyl-1,5-dioxa-spiro[5,4]-dec-8-yl]-trans-1-octene-3-ole-tetrahydropyranyl ether XIII 4.37 g of 1-[7-[(1,3-dithia-2-cyclopentyl)]-3,3-dimethyl-1,5-dioxa-spiro[5,4]-dec-8-yl]-trans-1-octene-3-ole were stirred in 30 ml of abs. ether with 4.4 ml of 2,3-dihydropyrane and some crystals of p-toluenesulfonic acid for 4 hours at room temperature. Then, 0.5 g of solid sodium carbonate was added, the mixture was stirred for 15 minutes, the sodium carbonate was filtered off and the organic phase was condensed under reduced pressure.

4.5 g of crude product were obtained which were filtered over a silica gel column of 12 cm height and 2 cm diameter in 90 parts of cyclohexane and 1 part of ethyl acetate. After distilling off the solvent 4.1 g of a light oil were obtained.

NMR spectrum:
5.3 – 5.65 ppm, 2 protons, broad signal
4.65 (c) ppm, 2 protons, broad signal
3.5 ppm, 4 [protons singlet
3.2 ppm, 4 protons, singlet In an analogous manner, there were prepared from the alcohols 8b, 8c, 8d and 8e described above the following tetrahydropyranyl ethers:

EXAMPLE 9b

1-[7-[(1,3-dithia-2-cyclopentyl)methyl]3,3-dimethyl-1,5-dioxaspiro-[5,4]-dec-8-yl]-trans-1-decene-3-ole-tetrahydropyranyl ether NMR spectrum:
5.3 – 5.65 ppm, 2 protons, broad signal
4.65 (c) ppm, 2 protons, broad signal
3.5 ppm, 4 protons, singulet
3.2 ppm, 4 protons, singulet

EXAMPLE 9c

1-[7-[(1,3-dithia-2-cyclopentyl)methyl]-3,3-dimethyl-1,5-dioxaspiro[5,4]-dec-8-yl]-3-(methylfuryl)-trans-1-propene-3-ole-tetrahydropyranyl ether

EXAMPLE 9d

1-[7-[(1,3-dithia-2-cyclopentyl)methyl]-3,3-dimethyl-1,5-dioxaspiro[5,4]-dec-8-yl]-3-cyclohexyl-trans-1-propene-3-ole-tetrahydropyranyl ether NMR spectrum:
5.3 – 5.65 ppm, 2 protons, broad signal
4.65 (c) ppm, 2 protons, broad signal
3.5 ppm, 4 protons, singlet
3.2 ppm, 4 protons, singlet

EXAMPLE 9e

1-[7-[(1,3-dithia-2-cyclopentyl)methyl]-3,3-dimethyl-1,5-dioxaspiro[5,4]-dec-8-yl]-3-(1,1-dimethyl-3-oxapentyl)-trans-1-propene-3-ole-tetrahydropyranyl ether.

NMR spectrum:
5.3 – 5.65 ppm, 2 protons, broad signal
4.65 (c) ppm, 2 protons, broad signal
3.5 ppm, 4 protons, singlet
3.2 – 3.3 ppm, 6 protons, singlet

EXAMPLE 10a

2-[3,3-dimethyl-8-[3-pentyl-3-tetrahydropyranyloxy-trans-1-octenyl]-1,5-dioxaspiro [5,4]-dec-7-yl]-acetaldehyde XIV 2.1 g of 1-[7-[(1,3-dithia-2-cyclopentyl)methyl]-3,3-dimethyl-1,5-dioxaspiro[5,4]-dec-8-yl]-trans-1-octene-3-ole-tetrahydro-pyranyl ether were heated in 25 ml of dimethyl formamide with 1.7 ml of methyl iodide, 3.4 g of calcium carbonate and 0.85 ml of $H_2O$ for 2 hours to 50° C, the calcium carbonate was filtered off, the precipitate was washed with acetone, the organic phase was condensed and dissolved in diethyl ether.

After washing with water and drying over $Na_2So_4$ the ether was distilled off.

1.7 g of a brownish oil were obtained.

UR spectrum: aldehyde bands at 1740 $cm^{-1}$.

EXAMPLE 10b

In an analogous manner, there were prepared from the thioacetals 9b – 9d the following acetaldehydes of the general formula XIV:

2-[3,3-dimethyl-8-[3-heptyl-3-tetrahydropyranyloxy-trans-1-propenyl]-1,5-dioxaspiro[5,4]-dec-7-yl]acetaldehyde UR spectrum The carbonyl band is practically identical with that obtained for 10a.

EXAMPLE 10c

2-[3,3-dimethyl-8-[3-(5'-methylfuryl)-3-tetrahydropyranyloxy-trans-1-propenyl]-1,5-dioxaspiro[5,4]-dec-7-yl]-acetaldehyde UR spectrum:
The carbonyl band was practically identical with that of 10a.

EXAMPLE 10d

2-[3,3-dimethyl-8-[3-cyclohexyl-3-tetrahydropyranyloxy-trans-1-propenyl]-1,5-dioxaspiro[5,4]-dec-7-yl]acetaldehyde UR spectrum The carbonyl band was practically identical with that of 10a.

EXAMPLE 10e

2-[3,3-dimethyl-8-[3-(1,1-dimethyl-3-oxapentyl)-3-tetrahydropyranyloxy-trans-1-propenyl]-1,5-dioxaspiro [5,4]-dec-7-yl]-acetaldehyde UR spectrum The carbonyl band was practically identical with that of stage 10a.

EXAMPLE 11a

7-[3,3-dimethyl-8-[3-pentyl-3-tetrahydropyranyloxy-trans-1-propenyl]-1,5-dioxaspiro [5,4]-dec-7-yl]-cis-5-heptenoic acid XV 640 mg of 80 % sodium hydride and 6 ml of dimethyl sulfoxide were heated for 1 hour to 65° C and, after cooling to room temperature, 4.7 g of 4-carboxybutyl-triphenylphosphonium-bromide in 8 ml of dimethyl-sulfoxide under argon were added and stirred for 20 minutes. To the red solution, 1.7 g of [3,3-dimethyl-8-[3-pentyl-3-tetra-hydropyranyloxy-trans-1-propenyl]-1,5-dioxaspiro-[5,4]-dec-7-yl]-acetaldehyde in 4 ml of dimethylsulfoxide were added dropwise and stirred for 15 hours at room temperature. 5% sodium hydrogen sulfate solution was added to that solution until pH 1 was reached, 50 ml of saturated sodium chloride solution were added and the mixture was esterified 3 times with 200 ml of diethyl ether, the combined organic phases were washed with water, dried and condensed.

3.6 g of crude product were obtained and chromatographed on silica gel (with a column of 12 cm height and 2 cm diameter). By elution with cyclohexane/ethyl acetate 9:1 and 8:2, 741 mg of pure compound were obtained.

NMR spectrum:
8 ppm; 1 proton; broad signal
5.2–5.6 ppm; 4 protons; broad signal
4.75 ppm; 1 proton; broad signal In an analogous manner the following acids were synthesized from the above described aldehydes of the general formula XIV, as they are obtainable from the experimental stages 10b, 10c, 10d and 10e:

EXAMPLE 11b

7-[3,3-dimethyl-8-[3-heptyl-3-tetrahydropyranyloxy-trans-1-propenyl]-1,5-dioxaspiro [5,4]-dec-7-yl]-cis-5-heptenoic acid
NMR spectrum:
8.6 ppm; 1 proton; broad signal
5.2–5.6 ppm; 4 protons; broad signal
4.75 ppm; 1 proton; broad signal

EXAMPLE 11c

7-[3,3-dimethyl-8-[3-(5-methylfuryl)-3-tetrahydropyranyl-oxy-trans-1-propenyl]-1,5-dioxaspiro [5,4]-dec-7-yl]-cis-5-heptenoic acid

EXAMPLE 11d

7-[3,3-dimethyl-8-[3-cyclohexyl-3-tetrahydropyranyloxy-trans-1-propenyl]-1,5-dioxaspiro [5,4]-dec-7-yl]-cis-5-heptenoic acid NMR practically identical with that of stages 11a and 11b

EXAMPLE 11e

7-[3,3-dimethyl-8-[3-(1,1-dimethyl-3-oxa-pentyl)-3-tetrahydropyranyloxy-trans-1-propenyl]-1,5-dioxaspiro [5,4]-dec-7-yl]-cis-5-heptenoic acid

EXAMPLE 12a

7-[2-(3-hydroxy-3-pentyl-trans-1-propenyl)-5-oxo-cyclopentyl]-cis-5-heptenoic acid (I)

Step α

740 mg of 7-[3,3-dimethyl-8-[3-pentyl-3-tetrahydropyranyl-oxy-trans-1-propenyl]-1,5-dioxaspiro [5,4]-dec-7-yl]-cis-heptenoic acid were dissolved in 20 ml of ethanol and stirred with 9.5 ml of 2% aqueous oxalic acid solution for 8 hours at room temperature, the solvent was extracted under reduced pressure, to the aqueous residue a saturated hydrochloric acid solution was added and the mixture was extracted three times with 150 ml of diethyl ether. The combined ether extracts were washed with water, dried and condensed. 579 mg of a light oil were obtained.

Step β

550 mg of the above oil were dissolved in 20 ml of dry acetone, stirred with 2 ml of a 0.5% solution of p-toluene-sulfonic acid in methylene chloride for 6 hours at 50° C and condensed under reduced pressure. The above residue was chromatographed over a silica gel column of 12 cm height and 2 cm diameter with cyclohexane/ethyl acetate/glacial acetic acid 90:10:1 and 80:20:1.

270 mg were obtained.
NMR spectrum:
7.05 ppm; 2 protons; broad singulet
5.3–5.7 ppm; 4 protons; broad signal
4.2 ppm; 1 proton; broad signal
7-[2-(3α-hydroxy-3-pentyl-trans-1-propenyl)-5-oxo-cyclopentyl]-cis-5-heptenoic acid
$R_f$ = 0.20 cyclohexane, ethyl acetate, glacial acetic acid 60:40:1
7-[2-(3β-hydroxy-3-pentyl-trans-1-propenyl)-5-oxo-cyclopentyl]-cis-5-heptenoic acid
$R_f$ = 0.24 cyclohexane, ethyl acetate, glacial acetic acid 60:40:1

In an analogous manner the following carboxylic acids were synthesized from the above described acids of the general formula XV as they were obtained from experimental stages 11b, 11c, 11d and 11e:

EXAMPLE 12b

7-[2-(3-hydroxy-3-heptyl-trans-1-propenyl)-5-oxo-cyclopentyl]-cis-5-heptenoic acid
NMR spectrum: practically identical with that of 12 a
7-[2-(3α-hydroxy-3-n-heptyl-trans-1-propenyl)-5-oxo-cyclopentyl]-cis-5-heptenoic acid
$R_f$ = 0.24 cyclohexane-ethyl acetate: glacial acetic acid 60:40:1
7-[2-(3β-hydroxy-3-n-heptyl-trans-1-propenyl)-5-oxo-cyclopentyl]-cis-5-heptenoic acid
$R_f$ = 0.27 cyclohexane:ethyl acetate:glacial acetic acid 60:40:1

EXAMPLE 12c

7-[2-[3-hydroxy-3-(5-methylfuryl)-trans-1-propenyl]-5-oxo-cyclopentyl]-cis-5-heptenoic acid

EXAMPLE 12d

7-[2-(3-hydroxy-3-cyclohexyl-trans-1-propenyl)-5-oxo-cyclopentyl]-cis-5-heptenoic acid
NMR spectrum: practically identical with 12 a
$R_f$ f  0.26 cyclohexane:ethyl acetate:glacial acetic acid 60:40:1

EXAMPLE 12e

7-[2-[3-hydroxy-3-(1,1-dimethyl-3-oxapentyl)-trans-1-propenyl]-5-oxo-cyclopentyl]-cis-5heptenoic acid
NMR spectrum: 3.3–3.7 ppm multiplet
7.05 ppm; 2 protons; broad signal
5.3–5.7 ppm; 4 protons; broad signal
4.05 ppm; 1 proton; broad signal
7-[2-[3α-hydroxy-3-(1,1-dimethyl-3-oxapentyl)-trans-1-propenyl]-5-oxo-cyclopentyl]-cis-5-heptenoic acid
$R_f$ = 0.24 cyclohexane:ethyl acetate:glacial acetic acid 60:40:1
7-[2-[3β-hydroxy-3-(1,1-dimethyl-3-oxapentyl)-trans-1-propenyl]-5-oxo-cyclopentyl]-cis-5-heptenoic acid
$R_f$ = 0.27 cyclohexane:ethyl acetate:glacial acetic acid 60:40:1

EXAMPLE 12f

7-[2-[3α-hydroxy-3-(3,3-4,4-tetrafluorocyclobutyl)-ethyl-trans-1-propenyl]-5-oxocyclopentyl]-cis-5-heptenoic acid $R_f$ = 0.15 cyclohexane:ethyl acetate:glacial acetic acid 60:40:1

7-[2-[3β-hydroxy-3-(3,3-4,4-tetrafluorocyclobutyl)-ethyl-trans-1-propenyl]-5-oxo-cyclopentyl]-cis-5-heptenoic acid $R_f$ = 0.29 cyclohexane:ethyl acetate:glacial acetic acid 60:40:1

In an analogous manner as described in the foregoing Examples, the following acids were synthesized:

EXAMPLE 13a

7-[2-(3β-hydroxy-3-cycloheptyl-trans-1-propenyl)-5-oxo-cyclo-pentyl]-cis-5-heptenoic acid $R_f$ = 0.25 cyclohexane:ethyl acetate:glacial acetic acid 60:40:1

7-[2-(3α-hydroxy-3-cycloheptyl-trans-1-propenyl)-5-oxo-cyclopentyl]-cis-5-heptenoic acid $R_f$ = 0.20 cyclohexane:ethyl acetate:glacial acetic acid 60:40:1

EXAMPLE 13b

7-[2-(3α-hydroxy-3-isopropyl-trans-1-propenyl)-5-oxo-cyclopentyl]-cis-5-heptenoic acid $R_f$ = 0.21 cyclohexane:ethyl acetate:glacial acetate acid 60:40:1

7-[2-[3β-hydroxy-3-isopropyl-trans-1-propenyl)-5-oxo-cyclopentyl]-cis-5-heptenoic acid $R_f$ = 0.26 cyclohexane:ethyl acetate:glacial acetate acid 60:40:1

EXAMPLE 13c

7-[2-(3α-3-n-propyl-trans-1propenyl)-5-oxo-cyclopentyl]-cis-5-heptenoic acid $R_f$ = 0.15 cyclohexane:ethyl acetate:glacial acetic acid 60:40:1

7-[2-(3β-hydroxy-3-n-propyl-trans-1-propenyl)-5-oxo-cyclopentyl]-cis-5-heptenoic acid $R_f$ = 0.21 cyclohexane:ethyl acetate:glacial acetic acid 60:40:1

EXAMPLE 14a

7-[2-(3-hydroxy-3-pentyl-trans-1-propenyl)-5-hydroxy-cyclopentyl]-cis-5-heptenoic acid, (general formula I)

50 mg of 7-[2-(3-hydroxy-3-pentyl-trans-1-propenyl)-5-oxo-cyclo-pentyl]-cis-5-heptenoic acid were dissolved in 20 ml of methanol and in the course of 1.5 hours three 50 mg portions of NaBH₄ were added. The reaction solution was adjusted to pH 7 with glacial acetic acid, the solvent was distilled off under reduced pressure, the residue was acidified in 1 ml of H₂O with 2 N hydrochloric acid to pH 1 and extracted three times with 150 ml portions of ether. The combined ether extracts were washed with water, dried and condensed.

40 mg. of acid were obtained.

NMR spectrum: 5.2–5.6 ppm; 4 protons; broad signal

In an analogous manner the following carboxylic acids of the general formula I were synthesized from the above described acids of the general formula I as they were obtained from experimental examples 12b, 12c, 12d and 12e:

EXAMPLE 14b

7-[2-(3-hydroxy-3-heptyl-trans-1-propenyl)-5-hydroxy-cyclopentyl]cis-5-heptenoic acid

EXAMPLE 14c

7-[2-[3-hydroxy-3-(5-methylfuryl)-trans-1-propenyl]-5-hydroxy-cyclopentyl]cis-5-heptenoic acid

EXAMPLE 14d

7-[2-(3-hydroxy-3-cyclohexyl-trans-1-propenyl)-5-hydroxy-cyclopentyl]cis-5-heptenoic acid

EXAMPLE 14e

7-[2-[3-hydroxy-3-(1,1-dimethyl-3-oxapentyl) trans-1-propenyl]-5-hydroxy-cyclopentyl]cis-5-heptenoic acid

We claim:

1. A compound of the formula

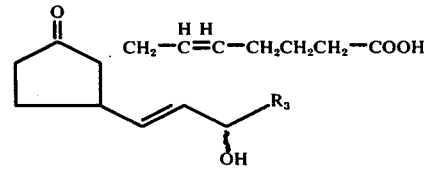

and physiologically acceptable salts thereof with organic and inorganic bases, wherein $R_3$ is linear or branched alkyl having 1 to 10 carbon atoms substituted by O-alkyl having 1 to 5 carbon atoms.

2. A compound as in claim 1 which is 7- 2-[3-hydroxy-3-(1,1-dimethyl-3-oxapentyl)-trans-1-propenyl]-5-oxo-cyclopentyl -cis-5-heptenoic acid.

3. A pharmaceutical composition for use as a bronchodilatant, a hypotensive agent, or as a diuretic, which composition comprises a therapeutically effective amount of a compound as in claim 1 in combination with a pharmaceutical carrier.

* * * * *